United States Patent [19]

Torchio

[11] Patent Number: 5,514,178
[45] Date of Patent: May 7, 1996

[54] PROSTHESIS FOR BODILY CANAL

[75] Inventor: Gérard Torchio, Verriere le Buisson, France

[73] Assignee: Synthelabo, Le Plessis Robinson, France

[21] Appl. No.: 250,577

[22] Filed: May 27, 1994

[30] Foreign Application Priority Data

Jun. 24, 1993 [FR] France .................................. 93 07693

[51] Int. Cl.⁶ .............................. A61F 2/04; A61F 2/02; A61M 29/00
[52] U.S. Cl. .............................. 623/12; 606/191; 604/8; 600/30
[58] Field of Search .................................. 623/1, 11, 12; 606/153, 191, 198; 600/30, 37; 604/8

[56] References Cited

U.S. PATENT DOCUMENTS

| | | | |
|---|---|---|---|
| 4,250,873 | 2/1981 | Bonnet | 128/7 |
| 4,531,933 | 7/1985 | Norton et al. | 604/8 |
| 4,721,095 | 1/1988 | Rey et al. | 623/12 |
| 4,955,859 | 9/1990 | Zilber | 604/8 |
| 4,994,066 | 2/1991 | Voss | 606/191 |
| 5,098,374 | 3/1992 | Othel-Jacobsen et al. | 604/8 |
| 5,269,802 | 12/1993 | Garber | 606/191 |
| 5,312,415 | 5/1994 | Palermo | 606/108 |
| 5,316,023 | 5/1994 | Palmaz et al. | 128/898 |

FOREIGN PATENT DOCUMENTS

| | | |
|---|---|---|
| 0481365 | 4/1992 | European Pat. Off. . |
| 1576374 | 8/1969 | France . |
| 2661603 | 11/1991 | France . |
| 321666 | 6/1920 | Germany . |
| 3836787 | 5/1990 | Germany ........................ 623/12 |
| 4104702 | 8/1992 | Germany ........................ 600/30 |
| 4130431 | 3/1993 | Germany . |
| 1771719 | 10/1992 | U.S.S.R. ........................ 623/12 |
| 2069339 | 8/1981 | United Kingdom ............ 623/12 |
| 2172203 | 9/1986 | United Kingdom . |

OTHER PUBLICATIONS

International Publication No. WO91/16005, published Oct. 31, 1991.
International Publication No. WO92/19310, published Nov. 12, 1992.
International Publication No. WO89/01798, published Mar. 9, 1989.
International Publication No. WO93/1824, published Jul. 22, 1993.

*Primary Examiner*—David Isabella
*Assistant Examiner*—Laura Fossum
*Attorney, Agent, or Firm*—Fisher, Christen & Sabol

[57] ABSTRACT

A prothesis intended to be introduced into a bodily canal which includes a flexible tube for preserving the normal passage cross section of the bodily canal and a holding device for immobilizing the flexible tube in position in the canal. The holding device is a tubular structure and is radially deformable so that it can pass from a first state in which its cross section is at most equal to that of the bodily canal into which it is to be introduced to a second state in which its cross section is such that the holding device bears on the wall of an orifice of the bodily canal emerging in a natural cavity. The holding device is linked at a distance to the flexible tube.

4 Claims, 5 Drawing Sheets

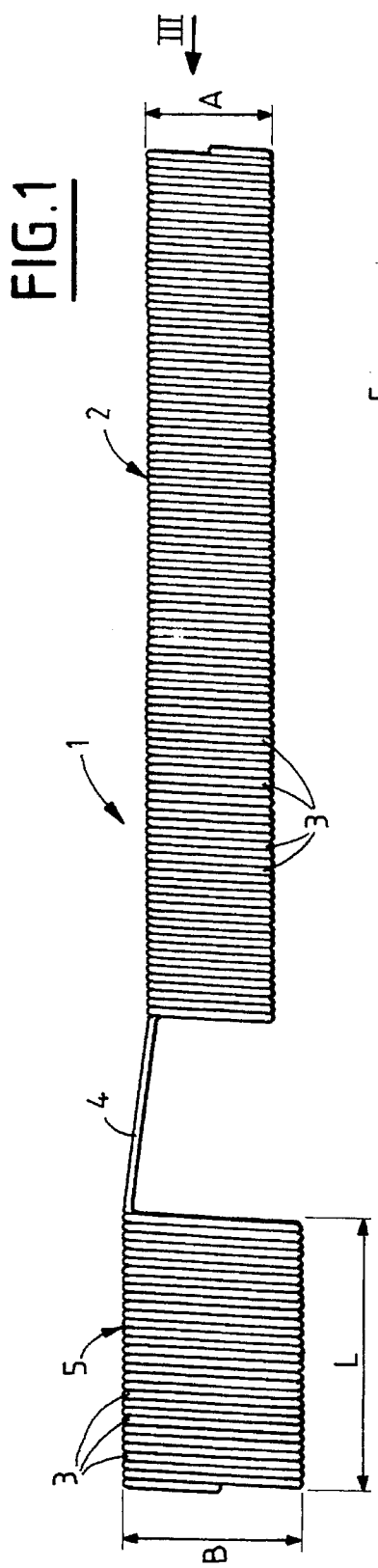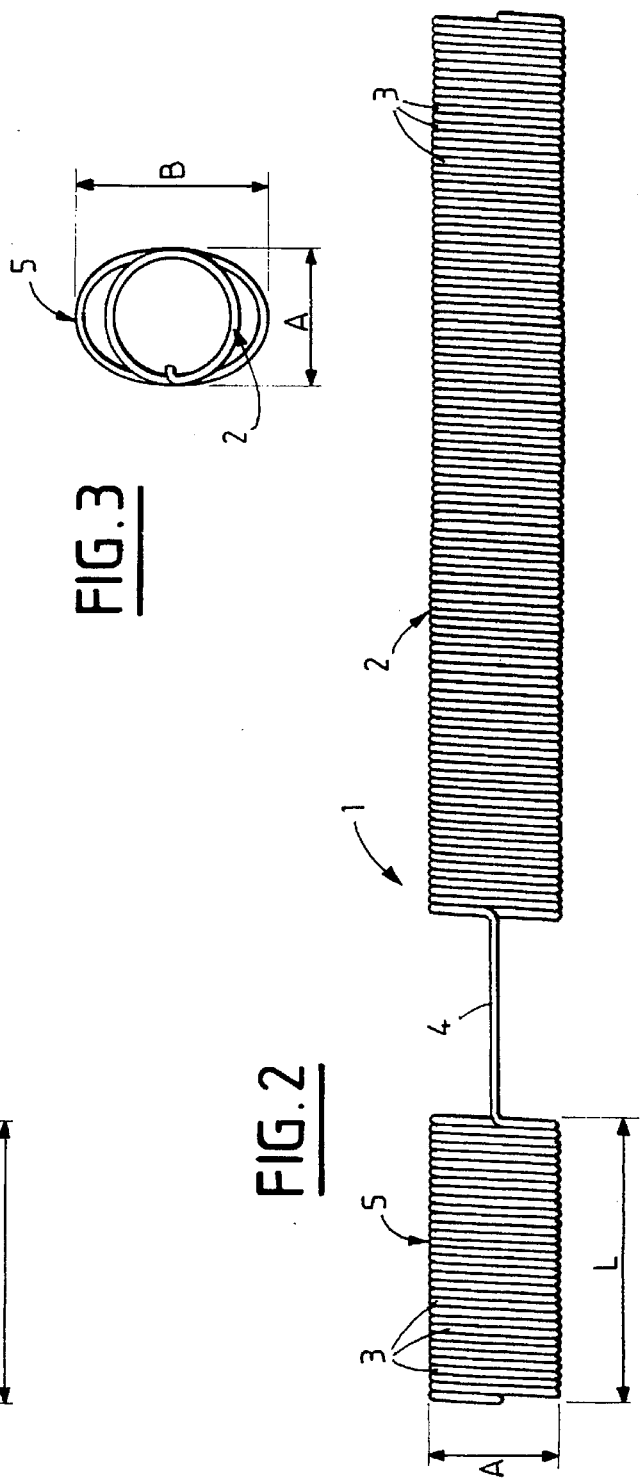

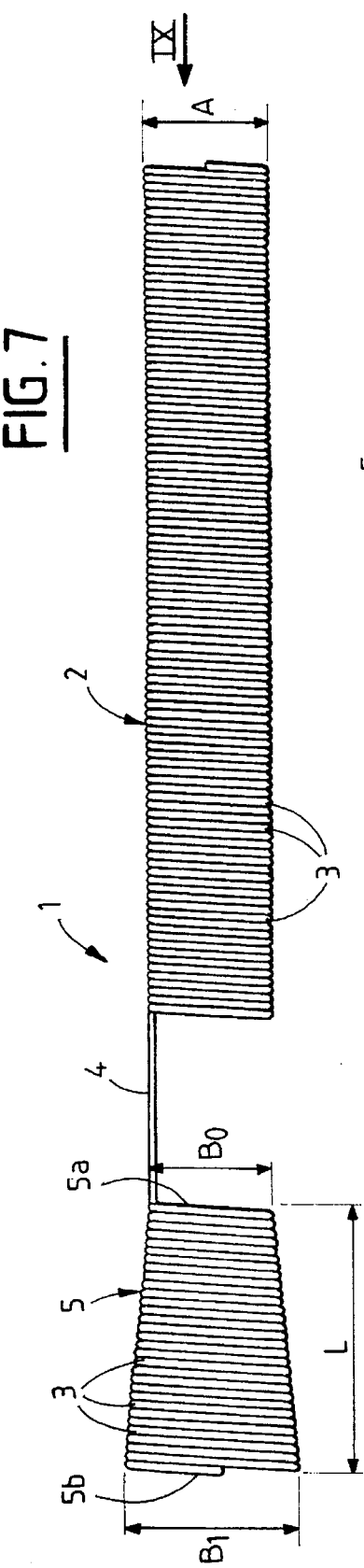
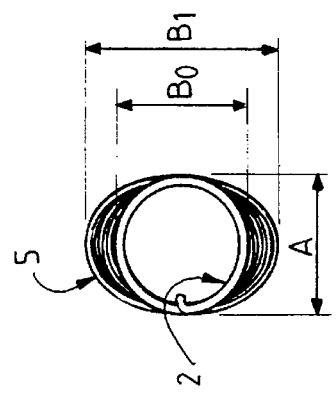
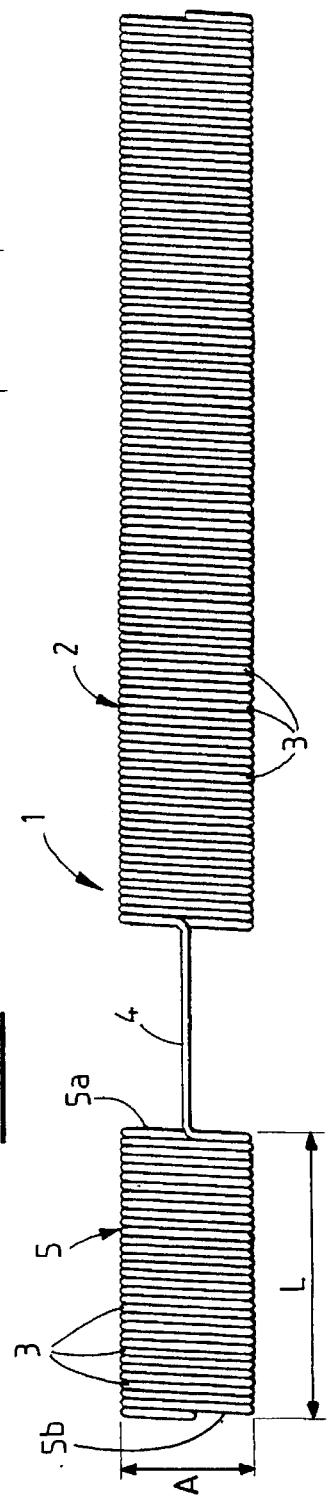

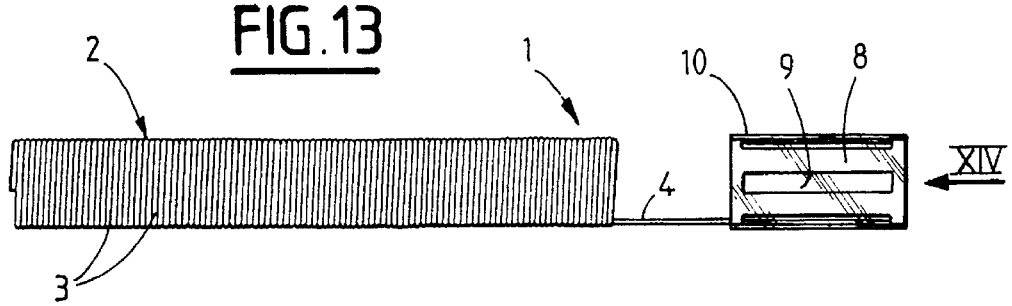
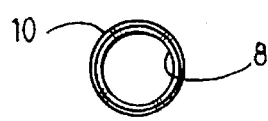
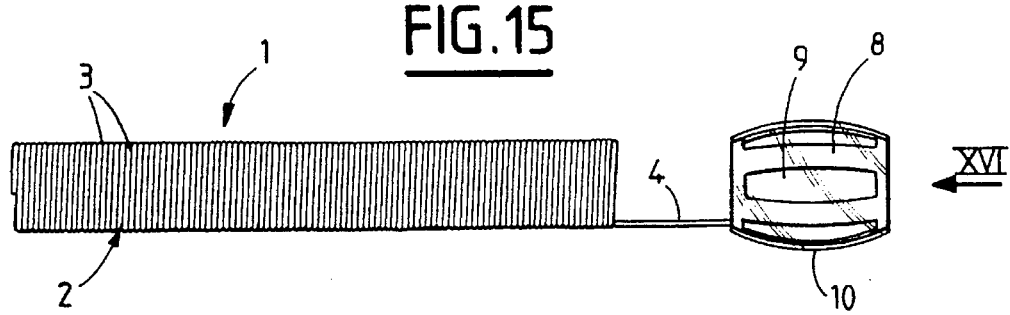
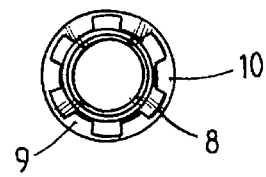
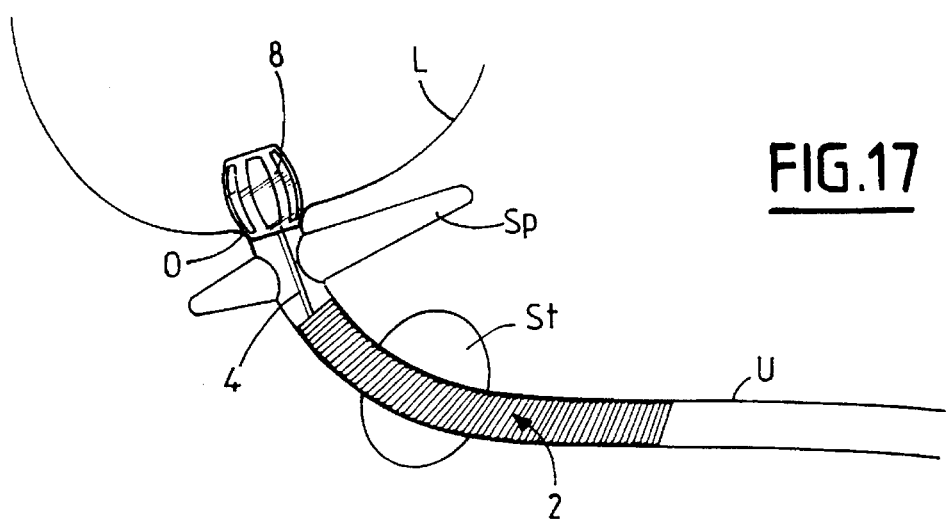

PROSTHESIS FOR BODILY CANAL

BACKGROUND OF THE INVENTION

1. Field of the Invention

The present invention relates to a prosthesis intended to be introduced into a bodily canal.

2. Description of the Related Art

For example, a removable urethral prosthesis is known for treating recurrent stenoses in the bulbo-membranous urethra. The object of this prosthesis is to hold the urethra open during healing after the urethrectomy and thus acts as a support for healing of the urethral wall. This prosthesis includes two parts, each in the form of a helical spring with contiguous turns. These two springs have the same diameter and different lengths and are joined to one another by a metal wire. The longer spring acts as the prosthesis proper, holding the urethra open at the diameter of the spring, whilst the shorter spring, connected to the distal end of the longer spring, allows the latter to be immobilized in position by fastening in the prostate. However, in certain cases, this prosthesis has a tendency to descend in the urethra because the fastening in the prostate by simple clamping is not always sufficient, for example when the prostatic urethra is too wide. In addition, when the prostate has been resected or after a prostatectomy, a prosthesis as defined hereinabove cannot be used.

SUMMARY OF THE INVENTION

The object of the present invention is to overcome these drawbacks, and relates to a prosthesis designed to be capable of being immobilized in position, in a positive manner, in a bodily canal.

For this purpose, the prosthesis intended to be introduced into a bodily canal, including a flexible tube intended to preserve the normal passage cross section of the bodily canal and constituting the prosthesis proper, and a holding device intended to immobilize said tube in position in said canal, said device being connected to the distal end of said tube by linkage means, while being arranged at a distance from said end, is noteworthy, according to the invention, in that the holding device consists of a radially deformable structure which can pass from a first state in which its cross section is at most equal to that of the bodily canal into which it is to be introduced, to a second-state in which its cross section is such that said structure can bear on the internal wall of the bodily canal, especially in the vicinity of the edge of an orifice of the bodily canal emerging in a natural cavity and, conversely, passing from said second state to said first state.

Thus, by virtue of this radially deformable structure of the holding device, the latter can be introduced, with the prosthesis proper, without problem into the bodily canal and, when the prosthesis is fitted, the holding device immobilizes the prosthesis (flexible tube) in position, in a positive manner, after being changed into its second state, by bearing and blocking on the bodily canal to whose diameter it can be adapted.

According to a first embodiment of the prosthesis of the invention, said structure is a helical spring having a cross section of oblong shape, the short dimension of which is at most equal to the internal diameter of the bodily canal.

In this case, for introduction into the bodily canal, the oblong turns of the spring may be inclined so that their long dimension only has, in the canal, a "height" corresponding to the internal diameter of the latter, including the tube for introducing the prosthesis. Once the prosthesis is in place, the oblong turns return into the initial position, which then makes it possible to positively immobilize the prosthesis in the canal.

The turns of said spring are preferably at least substantially contiguous.

According to a first variant of this embodiment, the oblong cross section of said spring is constant over its entire length whilst, according to a second variant, the long dimension of the oblong cross section of said spring increases progressively from its proximal end to its distal end.

In addition, said spring may be made from metal wire of medical quality.

According to a second embodiment of the prosthesis of the invention, said structure is a ring made of shape memory alloy, capable of radial expansion depending on the temperature to which it has been heated.

The ring has an initial diameter which allows it to be introduced into the bodily canal. By heating, once the prosthesis is fitted, the ring undergoes radial expansion making it possible to immobilize the prosthesis in position, according to the same principle as above.

Advantageously, said ring has longitudinal openings facilitating its radial expansion.

Said ring is preferably covered by a sheath of synthetic material, open at both ends, made in particular of silicone.

In addition, said flexible tube may be a helical spring, with at least substantially contiguous turns, of circular cross section, whilst said linkage means may consist of a metal wire.

The figures of the attached drawing will clearly explain how the invention may be embodied. In these figures, identical references denote similar elements.

BRIEF DESCRIPTION OF THE DRAWINGS

FIG. 1 is a side view of a first embodiment of a urethral prosthesis according to the invention.

FIG. 2 is a similar view to FIG. 1, but turned through 90° with respect to the latter.

FIG. 3 is a view along the arrow III in FIG. 1.

FIG. 7 is a side view of a variant of the first embodiment of a urethral prosthesis according to the invention.

FIG. 8 is a similar view to FIG. 7, but turned through 90° with respect to the latter.

FIG. 9 is a view along the arrow IX in FIG. 7.

FIG. 13 is a side view of a second embodiment of a urethral prosthesis according to the invention, the holding device of which, made of shape memory alloy, is in the retracted position.

FIG. 14 is a view along the arrow XIV in FIG. 13.

FIG. 15 is a similar view to FIG. 13, the holding device being, in this case, in the expanded position.

FIG. 16 is a view along the arrow XVI in FIG. 15.

FIG. 17 illustrates the urethral prosthesis according to FIGS. 13 and 15, fitted in the urethra of a patient.

DESCRIPTION OF THE PREFERRED EMBODIMENTS

Figure 6:
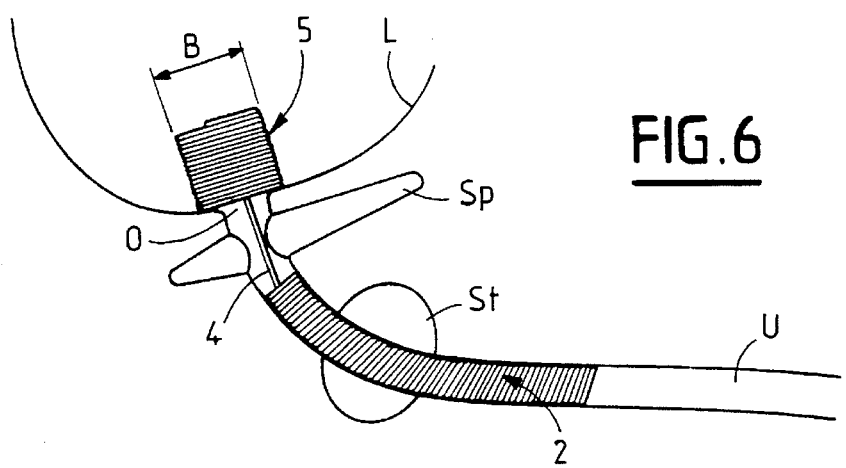
FIG. 6 illustrates the urethral prosthesis according to FIG. 1, fitted in the urethra of a patient.
Figure 10:
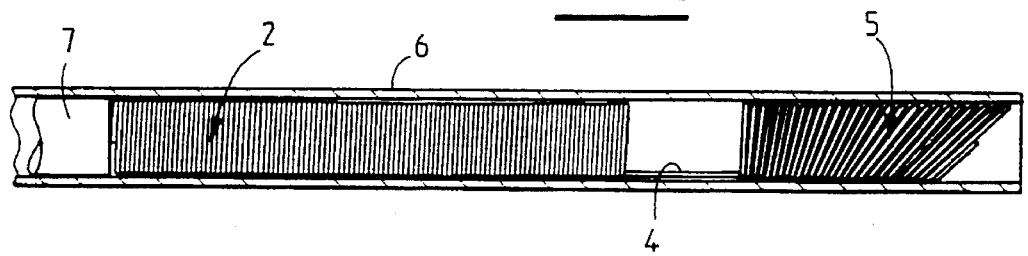
FIG. 10 shows the urethral prosthesis in FIG. 7 inserted into a fitting tube.

FIG. 1 represents, in side view, a first embodiment of a urethral prosthesis 1 according to the invention. The prosthesis 1 includes a first part 2 in the form of a first helical spring with contiguous turns 3, constituting the prosthesis proper, intended to be accommodated in the bulbo-membranous urethra U at the level of a stenosis St (FIG. 6). By way of non-limiting example and in order to give an order of magnitude, the spring 2 of circular cross section may have a constant external diameter of approximately 6.6 mm and a length of approximately 60 mm. The first spring 2 is joined, via a metal wire 4, to a second helical spring 5 with contiguous turns 3, intended to form the device for holding the spring 2 in the prostate or in the fascial sheath L of the prostate (FIG. 6). It will be noted that, as represented, the metal wire 4, which is intended to pass through the sphincter Sp (FIG. 6) and whose length may be of the order to 10 mm, may be formed in a single piece with the first and second springs and that, moreover, the first spring 2, the metal wire 4 and the second spring 5 are advantageously made of a stainless metal of medical quality.

The second spring 5 is shorter than the first spring 2 and may have, for example, a length of approximately 15 mm. In addition, according to the invention and in contrast to the first spring 2 which has a circular cross section (FIG. 3), the second spring 5 has an oblong shape in cross section (FIG. 3), which is substantially elliptical or in the shape of an "athletics track". By way of non-limiting example, the long "axis" A of this "ellipse" may have a length of approximately 10 mm and its short "axis" B a length of approximately 6.6 mm. It will be noted that, in this case, this oblong cross section is constant over the entire length L of the second spring 5.

Figure 4:
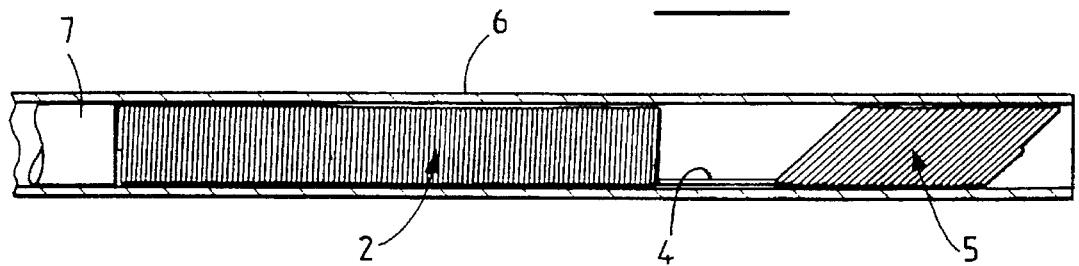
FIG. 4 shows the urethral prosthesis in FIG. 1 inserted into a fitting tube.
Figure 5:
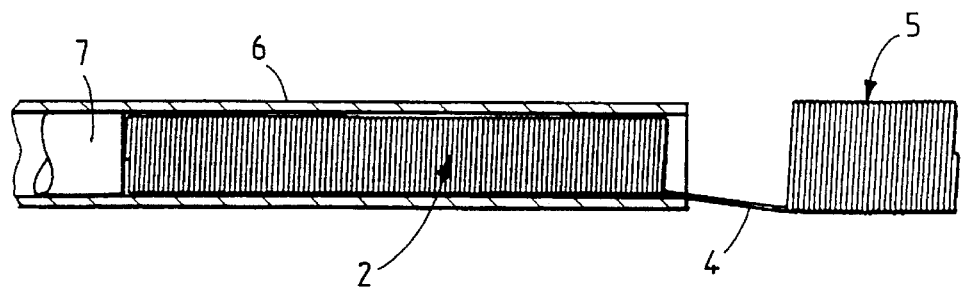
FIG. 5 is a similar view to FIG. 4, but with the holding device out of the tube.

As shown in FIG. 4, the prosthesis 1 can be introduced into the fitting tube 6 (constituting standard equipment with a determined internal diameter corresponding to the external diameter of the spring 2) by inclining the oblong turns of the spring 5. This is possible because the "width" of the oblong cross section of the spring 5 is equal to the diameter of the spring 2. At the moment of fitting the prosthesis in the urethra, using the pusher 7, the "inclined" spring 5 in the tube returns to its initial shape when leaving this tube (see FIG. 5).

As is seen in FIG. 6, once the fitting tube 6 has been withdrawn, the length B of the long "axis" of the cross section of the spring 5 is sufficient to hold the spring 2 in position in the urethra U at the level of the stenosis St, by bearing on the edge of the opening 0 of the urethra U emerging in the fascial sheath L of the prostate.

The variant of the first embodiment of the urethral prosthesis 1, shown in FIGS. 7 to 12, differs from the prosthesis in FIGS. 1 to 6 only in that, in this case, the second spring 5 has a substantially frustoconical shape with a cross section which is also substantially elliptical or in the shape of an "athletics track", but the long "axis" B of which increases progressively (for example from 6.6 mm to 10 mm) from the proximal end 5a (Bo) of the spring 5 facing the spring 2 to its opposite distal end 5b (B1), whilst the short "axis" A (equal to the diameter of the spring 2) remains constant over the entire length L of the spring 5 (see FIGS. 7 to 9). It will be noted that, in fact, Bo is equal to A at the end 5a.

Figure 11:
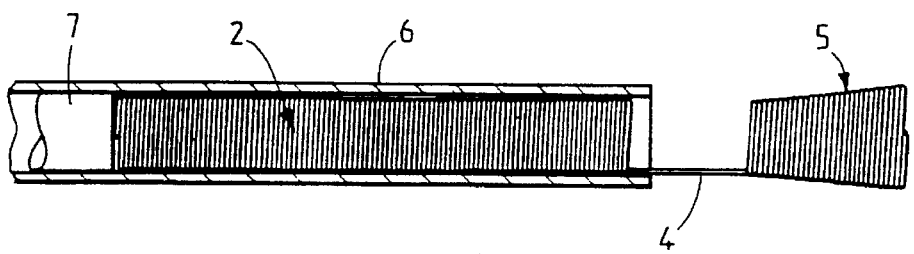
FIG. 11 is similar to FIG. 10, but with the holding device out of the tube.

This configuration of the second spring 5 also allows introduction of the prosthesis 1 into the fitting tube 6 (FIG. 10) by inclining the oblong turns of the spring 5, which returns to its initial position when leaving the tube 6 under the action of the pusher 7 (FIG. 11).

Figure 12:
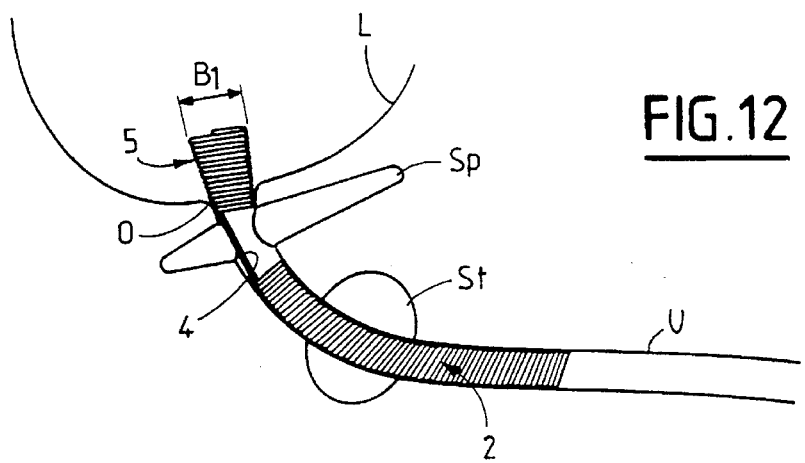
FIG. 12 illustrates the urethral prosthesis according to FIG. 7, fitted in the urethra of a patient.

Furthermore, as is seen in FIG. 12, the spring 2 is then held in position in the urethra U at the level of the stenosis St, by bearing of the spring 5 in the vicinity of the opening 0 of the urethra U emerging in the fascial sheath L of the prostate, the proximal end part of the spring 5 being slightly pushed into the urethra U until it is blocked when the increase in the length B toward the distal end of the spring 5 is sufficient.

In the second embodiment of the urethral prosthesis 1, represented in FIGS. 13 to 17, the helical spring 2 is again found, with contiguous turns 3, circular cross section and constant diameter, intended to form the prosthesis proper in the urethra U at the level of the stenosis St. However, in this case, the spring 2 is joined, via a metal wire 4 intended to pass through the sphincter Sp, to a device 8 for holding the spring 2 in position in the urethra U at the level of the stenosis St, which device consists of a ring 8 made of shape memory alloy, having longitudinal openings 9 facilitating its radial expansion, and capable of being covered by a sheath 10 of synthetic material, in particular of silicone, open at both ends in order to guarantee passage of fluids through the ring 8. In the expanded state, the ring 8 guarantees holding in position of the spring 2 by bearing in the vicinity of the edge of the opening O of the urethra U emerging in the fascial sheath L of the prostate (FIG. 17).

The purpose of the openings 9 is to facilitate the radial expansion of the ring 8 and to increase the percentage increase in diameter of the ring. If there were no such openings, the radial expansion percentage of the ring would be approximately 8%, whilst, by providing the openings 9, it is possible to reach radial expansion percentages which can be up to 100% or even 200%, because the expansion is, in this case, a function of the length of the tube forming the ring 8 and of the openings and no longer of the nature of the material employed.

In addition, in order to prevent any proliferation of tissue inside of the ring, the latter may be covered with a silicone sheath which also ensures better biocompatibility of the whole.

When fitting the prosthesis, the shape memory alloy ring has the same external diameter as the rest of the prosthesis. When the prosthesis is in place in the urethra, the ring can then be heated to cause its radial expansion in the fascial sheath of the prostate. Various types of heating may be used: liquid source, laser beam, high-frequency induction, insulated electrical heating sleeve. For withdrawing the prosthesis, another characteristic of shape memory alloys is used, which become malleable at temperatures of approximately 10° to 15° C. In situ cooling will need to be carried out before withdrawal of the prosthesis.

The shape memory alloys may be selected, without limitation, from the families: Ti Ni, Cu Zn Al, Cu Al Ni or Fe Mn.

The shape memory alloy will furthermore be chosen to exhibit austenitic hot shape resumption at a temperature greater than that of the human body. In order to facilitate manipulation and to respect the surrounding tissues, the transformation start temperature (As) will be chosen in the vicinity of 37° C. and the transformation end temperature (Af) as close as possible to the transformation start temperature (appearance of austenite). In order to make it possible to withdraw the shape memory alloy ring, in situ fluid cooling is provided. In order to facilitate manipulation and to respect the surrounding tissues, the temperature for which any trace of austenitic phase has disappeared (Mf) will be chosen as high as possible (reduction of hysteresis). As soon as it is cooled to a temperature less than the temperature Mf, the ring returns to being malleable and can be withdrawn.

It will moreover be noted that the use of a shape memory alloy ring having the superelasticity characteristic at the temperature of the human body makes it possible to insert the ring without heating constraint and to withdraw it without cooling. A device for clamping the ring to its minimum diameter will be used during the fitting of the prosthesis, as well as for extracting the ring.

It is obvious that the invention is not limited to the embodiments described of a urethral prosthesis. In fact, the holding device of the invention may be used for holding and immobilizing in position any similar prosthesis in a bodily canal of similar type.

I claim:

1. A prosthesis intended to be introduced into a bodily canal having a passage cross section, said prosthesis comprising:

a flexible tube intended to preserve said passage cross section of the bodily canal, a holding device intended to immobilize said tube in position in said canal, said holding device being connected to one end of said tube by linkage means, while being arranged at a distance from said end, said holding device being radially deformable and being able to pass from a first cross section which is at most equal to said passage cross section, to a second cross section which is such that said holding device bears on a wall of an orifice of the bodily canal emerging in a natural cavity, and said holding device being a tubular helical spring made of turns at least substantially contiguous, said tubular helical spring having a length of several millimeters, said helical spring having a cross section of oblong shape, a short dimension of the oblong cross section of the said tubular helical spring being at most equal to said passage cross section, and a long dimension of the oblong cross section of said tubular helical spring being greater than the said passage cross section.

2. The prosthesis as claimed in claim 1, wherein the oblong cross section of said spring is constant over its entire length.

3. The prosthesis as claimed in claim 1, wherein the long dimension of the oblong spring increases progressively from an end closest to the flexible tube to an end farthest from the flexible tube.

4. The prosthesis as claimed in claim 1, wherein said spring is made from metal wire of medical quality.

* * * * *